Figure 1:
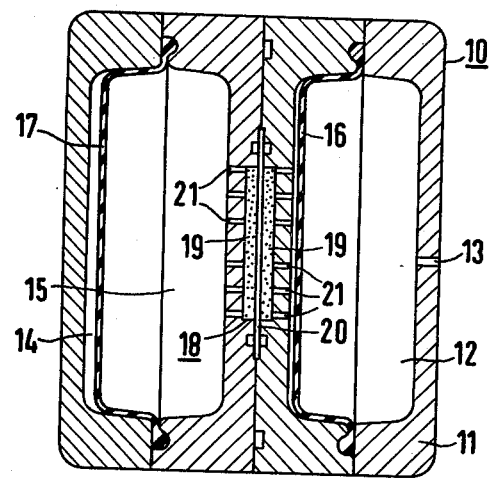

United States Patent [19]

Kühl et al.

[11] 4,140,122
[45] Feb. 20, 1979

[54] IMPLANTABLE DOSING DEVICE

[75] Inventors: Dieter Kühl, Möhrendorf; Günter Luft, Lauf, both of Fed. Rep. of Germany

[73] Assignee: Siemens Aktiengesellschaft, Berlin and Munich, Fed. Rep. of Germany

[21] Appl. No.: 802,963

[22] Filed: Jun. 2, 1977

[30] Foreign Application Priority Data

Jun. 11, 1976 [DE] Fed. Rep. of Germany ....... 2626348

[51] Int. Cl.² ............................................. A61M 31/00
[52] U.S. Cl. ................................... 128/260; 128/213; 128/272; 424/19
[58] Field of Search ............... 128/130, 213, 272, 260; 424/19, 228

[56] References Cited

U.S. PATENT DOCUMENTS

| 3,896,806 | 7/1975  | Wichterle      | 424/19  |
| 3,987,790 | 10/1976 | Eckenhoff et al. | 128/130 |
| 4,003,379 | 1/1977  | Ellinwood      | 128/260 |
| 4,016,880 | 4/1977  | Theeuwes et al. | 128/260 |
| 4,034,756 | 7/1977  | Higuchi et al.  | 128/260 |

Primary Examiner—Leland A. Sebastian
Attorney, Agent, or Firm—Kenyon & Kenyon, Reilly, Carr & Chapin

[57] ABSTRACT

The invention relates to an implantable dosing device for the continuous release of medication in the human or animal body, comprising a medicine reservoir of variable volume and a propellant chamber of variable volume tensionally connected to the medicine reservoir, as well as flow-control means. According to the invention, an electro-osmotic control valve with an ion exchange diaphragm arranged between two porous electrodes is provided for the flow control in such a dosing device.

8 Claims, 4 Drawing Figures

IMPLANTABLE DOSING DEVICE

BACKGROUND OF THE INVENTION

The invention relates to an implantable dosing device for the continuous release of medication in the human or animal body, comprising a medicine reservoir of variable volume and a propellant chamber of variable volume tensionally connected to the medicine reservoir, as well as flow control means.

In a number of diseases it is necessary to dispense medication to the patient over extended periods of time. The dispensing of Insulin in the case of diabetes, corticosteroids in the case of rheumatic diseases or cytostatica in the case of cancer are examples of such medications. These medications have heretofore been delivered to the patient's body predominantly orally or by injection at certain time intervals. Such delivery of medication is, therefore, intermittent and is only imperfectly matched to the actual requirement of the patient. With many medications, it is in addition very important that the dosing is very accurate, as an excess, as well as deficiency, can have detrimental effects.

Accordingly, a number of devices for delivering medication to the human or animal organism have already been developed, the purpose of which is to allow better dosing of medication. Of these devices, mechanical pumping systems have the disadvantage that they have movable parts such as gears and valves which are subject to wear in operation and in most cases do not meet the requirements which are desired as to dosing accuracy, service life and tightness.

An implantable dosing device, a so-called infusion pump, is known, which has in a housing two chambers which are separated from each other by a liquid- and vapor-tight intermediate phase forming a pressure connection (German Offenlegungsschrift No. 2,124,062 or U.S. Pat. No. 3,731,681). The first of these two chambers, which has an inlet opening which is closed-off liquid- and vapor-tight, is partially filled with a stable, volatile liquid, which exerts a vapor pressure which is higher than one atmosphere at physiological temperatures. Such liquids are, for example, perfluoropentane, tetramethyl silane, ethyl ether and methylformiate. The second chamber has an inlet opening which is closed-off liquid-tight, and at least one release opening which is in direct fluidic connection with a flow-regulating resistance element. The flow control, which is also in direct fluidic connection with a line which leads to at least one infusion location, is preferably a capillary tube; however a porous plug or a filter may also be used.

In this known dosing device, the medium to be infused is transported by the vapor pressure of a liquid. As this vapor pressure is constant for a given (body) temperature, a substantially constant flow velocity will in general adjust itself which, while dependent on the type of flow regulator used, is also predetermined by its nature. Thus, the delivery of the medicine to the body cannot be controlled or regulated which is disadvantageous since regulation is typically necessary or desirable. For example, in the case of diabetics, the Insulin requirement is usually greater during the day than during the night. In addition, the known infusion pump has the disadvantage that the pumped volume depends on the body temperature, i.e., the pumping is not uniform if there are temperature variations. In the event of fever, there is also the danger of overdosing and thus, possibly, danger to the patient.

SUMMARY OF THE INVENTION

It is therefore an object of the invention to develop an implantable dosing device of the type mentioned at the outset comprising a medication reservoir, a propellant chamber and flow control means, in such a manner that the medicine release to the body can be controlled or regulated and thus adapted to the demand at any time.

According to the invention, this is achieved by providing an electro-osmotic control valve with an ion exchange diaphragm arranged between two porous electrodes for flow control.

In such a regulating valve, liquid is transported through the electrodes and through the ion exchange diaphragm when current flows. For example, negative charges are fixed at the pore walls of the ion exchange diaphragm, and the mobile positive ions, which are necessary for reasons of electro-neutrality, then travel in the electric field and take along the liquid by friction.

In addition to the advantage that the implantable dosing device according to the invention can be controlled or regulated, the device, is also not influenced by changes of the body temperature insofar as its operation and effectiveness are concerned. This is due to the fact that the medicine transport due to the gas pressure of a propellant in the propellant chamber is superimposed, i.e., regulated, by the amount of liquid which passes through the ion exchange diaphragm electro-osmotically by virtue of the electric field between the two electrodes. The dosing device according to the invention therefore makes possible not only a continuous, but also a uniform release of small amounts of medication to the human or animal organism. In addition, the medicines are dosed accurately and free of disturbances over an extended period of time.

Within the scope of the present description medication is understood in the broadest sense to include any substance which serves in any way to improve, restore or maintain a patient's health. Thus medication includes for example, hormones, enzymes and vitamins.

As compared to dosing devices such as disclosed in German Offenlegungsschrift No. 2,239,432 or U.S. Pat. No. 3,894,538, the device according to the invention has the advantage that it requires relatively little electric energy. In the above devices, which comprise a medicine reservoir of variable volume and a liquid chamber tensionally connected thereto, the volume of the liquid chamber can be varied by liquid which is transported by electro-osmosis through an ion exchange diaphragm due to an electric field between two porous electrodes. Here, electric energy must, therefore, be spent for transporting the medication as well as for controlling the flow of liquid, i.e., for the total pumping process. In the dosing device according to this invention, on the other hand, electric energy is required only for controlling the release of medication, while the transport per se, which accounts for the major part of the energy required, is effected by the propellant.

In the simplest embodiment of the dosing device, the medicine reservoir is separated from the propellant chamber by an elastic partition and the electro-osmotic regulating valve is arranged at the medicine reservoir. In this embodiment, which is distinguished by a small overall volume, the medicine reservoir contains, besides the medication proper, the liquid which is required for carrying out the osmosis, in the form of a physiological saline solution. It is thus necessary that the medication used be water-soluble and have a low-molecular structure so it can pass through the ion exchange diaphragm together with the ions and their hydrate shells travelling due to the electric field. In this manner, blood-pressure depressants, for example, can be fed to the body. As in this embodiment of the dosing device, the medication also comes into contact with the electrodes and it therefore must not be attacked by the electrode material.

In a particularly preferred embodiment of the dosing device, a liquid chamber of variable volume is provided between the propellant chamber and the medicine reservoir. This liquid chamber is separated from the propellant chamber and the medicine reservoir by respective partitions, and the electro-osmotic control valve is arranged in the liquid chamber. In this embodiment, the liquid used for the electro-osmosis is hermetically sealed from the medicine or the medicine solution and the medicine or its solution does not come into contact with the electrode material. Therefore, the medicine is not subject to any limitations and the liquid used in the liquid chamber need not meet the requirement of body compatibility. Thus, an electrolyte solution other than a physiological saline solution may also be used instead.

In the electro-osmotic regulating valve of the dosing device according to the invention, silver/silver halogenide electrodes are preferably used as the electrodes, particularly silver/silver chloride (Ag/AgCl) electrodes. Such electrodes are distinguished by a low polarization voltage. Other reversible electrodes such as Ni/NiO electrodes may also be used, however.

In the propellant chamber of the dosing device according to the invention, a volatile liquid is advantageously used as the propellant. A constant gas pressure then adjusts itself at a given temperature to permit the uniform transport of the medication in a simple manner. The volatile liquid in the propellant chamber is preferably a low hydrocarbon, such as dichlorofluoro methane ($CHCl_2F$), trichlorofluoromethane ($CCl_3F$), chloroethane ($C_2H_5Cl$) (ethyl chloride) or 1,2 dichloro-1,1,2,2-tetrafluoroethane ($CClF_2CClF_2$). At body temperature these substance have a vapor pressure of between about 1.5 and 3 bar. However, other propellants such as ethylamine ($C_2H_5NH_2$) may also be used (vapor pressure about 2.2 bar).

An inert gas under pressure, particularly nitrogen, can also serve as the propellant. The gas pressure is chosen here between about 1 and 3 bar. In such a system, however, the gas pressure decreases with time. A substantially constant gas pressure can be obtained, however, if the propellant is a material storing gas under pressure. Such materials are in particular hydrides, the hydrides of transition metals and transition metal compounds being preferable. In the gas phase above such compounds, a constant gas pressure adjusts itself at a given temperature. Examples of hydrogen-storing hydrides are the following compounds: $PrCo_5$ (hydrogen pressure at room temperature: 0.6 bar), $NdCo_5$ (0.8 bar) and $LaNi_5$ (2.5 bar).

In the dosing device according to the invention, a gas serving as the propellant can advantageously also be developed exclusively during the operation of the dosing device. An electrochemical cell can be used for this purpose. In this embodiment, the propellant chamber contains an electrolyte, and two electrodes separated from each other by a hydrophilic diaphragm are further provided. The gas can be developed particularly advantageously by means of a reversibly operating cell with a hydrogen-storing electrode system. For this purpose palladium-hydrogen electrodes are particularly well suited. At a pressure of 1 bar, the storage capacity of such electrodes is, for example, 63.5 ml hydrogen for 1 g palladium. In such a system, it is preferable that at least one of the two electrodes, i.e., the anode, is a palladium-hydrogen electrode. In the operation of the electrochemical cell, the hydrogen dissolved in the palladium is reacted electrochemically at the anode, i.e., dissolved and transported as an $H^+$-ion through the diaphragm to the cathode. At the cathode, a reduction then takes place, that is, hydrogen is developed. This gaseous hydrogen serves as the propellant which acts on the elastic partition between the propellant chamber and the medicine reservoir or the liquid chamber, respectively. The reversibly operating system requires only little power, a small constant electric current being sufficient to obtain uniform gas development. The power required is generally about 10 to 20 $\mu W$. Such an arrangement has the additional advantage of permitting control of the pressure of the propellant.

The electrodes arranged in the propellant chamber may also serve for the electrolysis of water, for which purpose platinum electrodes, for example, are used. Here, oxygen is developed at the anode and hydrogen at the cathode. Such a system has the advantage of making two gases available as propellants. Accordingly, the propellant chamber can be provided with an elastic partition on each side, and a medicine reservoir can be arranged at each of these partitions. However, the relatively large amount of power required, about 100 to 150 $\mu W$, is noted as a disadvantage.

Figure 2:
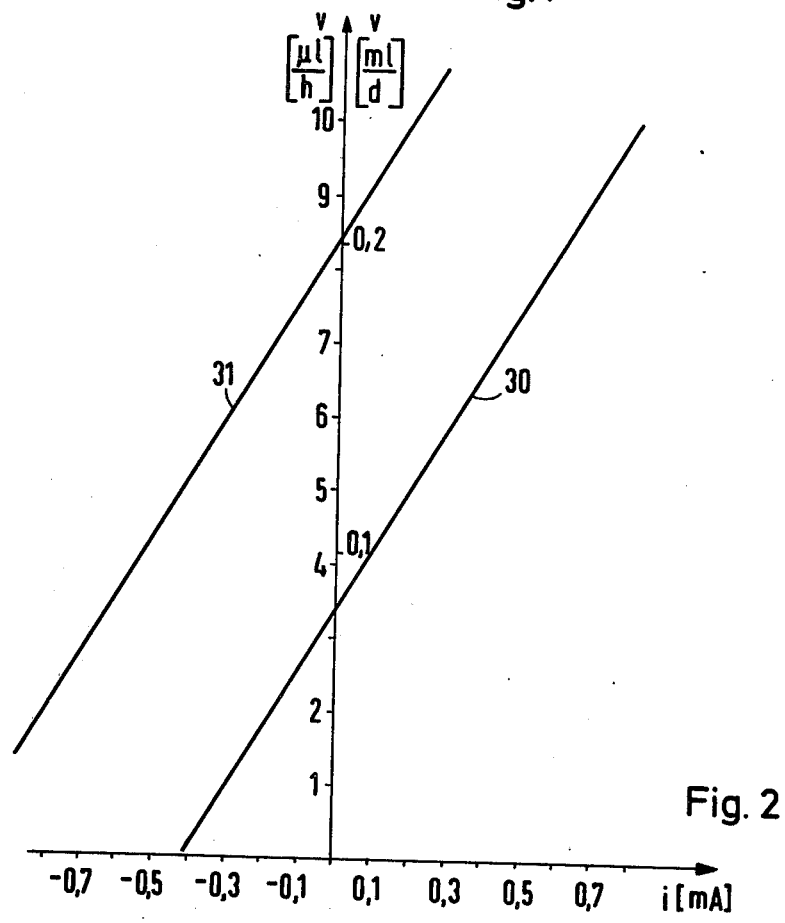
Figure 3:
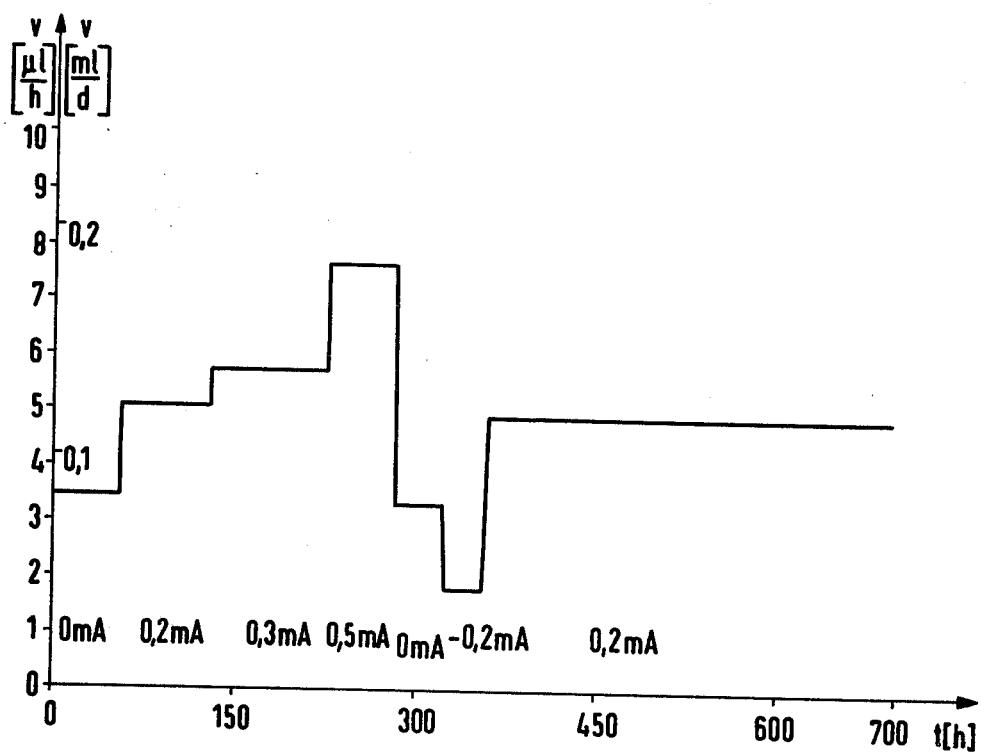

The invention will be explained in still further detail with reference to embodiment examples and several figures, where FIG. 1 shows a preferred embodiment of the dosing device according to the invention;

FIG. 2, the transport-vs-current diagram of such a dosing device;

FIG. 3, its control behavior; and

Figure 4:
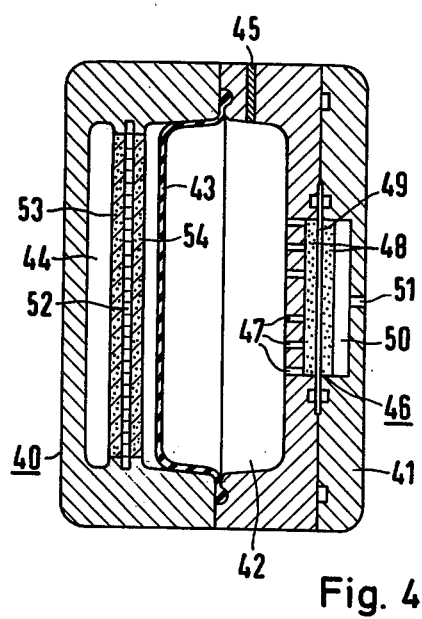

FIG. 4 shows a further embodiment of the dosing device.

In FIG. 1, a preferred embodiment of the dosing device according to the invention is shown in a cross section. The dosing device 10 comprises within a housing 11 a medicine reservoir 12 which is provided with a discharge opening 13; a propellant chamber 14; and a liquid chamber 15. The medicine reservoir 12 is separated from the liquid chamber 15 by an elastic partition 16 and the propellant chamber 14 is separated from the liquid chamber by an elastic partition 17. An electro-osmotic regulating valve 18 is arranged inside the liquid chamber 15. In the mechanical design shown here, as will be seen from FIG. 1, the liquid chamber 15 is divided by the housing 11 practically into two subchambers, between which the regulating valve 18 is arranged. The regulating valve consists of two porous Ag/AgCl electrodes 19, which are arranged on both sides of an ion exchange diaphragm 20. The two subchambers of the liquid chamber 15 are connected to the electrodes 19 by way of canals 21.

In the propellant chamber 14 of the dosing device 10 there is a liquid-and-vapor mixture of a volatile liquid serving as the propellant, which has constant gas pressure at a given temperature. The propellant is advantageously chosen so that the pressure exerted by the liquid at body temperature is in the range of about 1 to 3 bar, since if there is a leak in the dosing device, the danger is less with low pressure. In addition, the design can be kept advantageously small. As the propellant, trichlorofluoromethane $CCl_3F$, which has a vapor pressure of about 1.6 bar at body temperature (37° C.), is preferably utilized.

The vapor pressure of the liquid in the propellant chamber 14, which acts on the elastic partition 17, pushes the solution in the liquid chamber, for example, a diluted saline solution, via the canals 21 through the electrodes 19 and the ion exchange diaphragm 20. With its hydrodynamic permeability, the ion exchange diaphragm insures that a constant flow of liquid can pass through it. By this flow of liquid, the partition 16 between the liquid chamber and the medicine reservoir, which consists, like partition 17, of an elastic silastic diaphragm, is moved toward the medicine reservoir 12. In the process, the medicine contained in the medicine reservoir is pushed out through the discharge opening 13. The discharge opening is advantageously closed-off by a plug with fine pores in order to prevent back-diffusion of body fluid into the medicine reservoir or uncontrolled discharge of the medication from the reservoir.

In the dosing device according to the invention, the flow of liquid passing through the ion exchange diaphragm can be controlled by the electrode system, as an ion flow can be superimposed on the liquid flow. This ion flow is controlled or regulated by way of the two electrodes. The liquid flow caused by the pressure of the propellant can then be amplified or reduced by the electro-osmotic liquid transport. If an anion exchange diaphragm is used in the dosing device, then the electric current must be in a direction opposite the liquid flow in order to decrease the latter, and it must have the same direction to increase it. The situation is the opposite if a cation exchange diaphragm is used.

It is an advantage of the embodiment according to FIG. 1 that this dosing device is closed-off against the body and, therefore, the liquid in the liquid chamber 15 can be chosen at will. Physiological saline solution is therefore not required, but other electrolyte solutions may also be used, for example, phosphate buffer solutions.

The control and transport properties of such an embodiment of the dosing device were investigated with a measuring cell which was subjected to constant gas pressure. Different ion exchange diaphragms were used for the investigations, which differed with respect to hydrodynamic permeability. The ion exchange diaphragms were clamped between two porous Ag/AgCl electrodes, the area of which was 5 cm². This area also forms the passage area of the liquid through the ion exchange diaphragm. The electrolyte was a 0.9-% aqueous sodium chloride solution.

In FIG. 2, the transport-vs-current diagram is shown which was obtained when an anion exchange diaphragm (Nepton A 111 BZL 183 manufactured by Ionics), 0.6 mm thick, was used which has a hydrodynamic permeability of $1 \times 10^{-9}$ cm³/p.s (cm³/g.s). It is evident from the diagram that the pump output v, at 20° C., is about 3.5 $\mu$l/hr. for a current $i = 0$ mA and a pressure of 1.5 bar (Curve 30), i.e., less than 0.1 ml/day; at 2.0 bar (Curve 31), the pump output is about 8.5 $\mu$l/hr. corresponding to about 0.2 ml/day. The power consumption of the dosing device, which is zero for $i = 0$, rises, at 1.5 bar, only from 2.0 $\mu$W at 0.2 mA to 4.5 $\mu$W at 0.3 mA to 20 $\mu$W at 0.5 mA. The energy consumption of such a dosing device is therefore extremely small and this dosing device differs advantageously from other similar devices with respect to energy consumption.

The pump output of the dosing device according to the invention can be varied within relatively wide limits. Apart from the factors of current density and pressure, which influence the pump output, as seen in FIG. 2, different pump outputs are also obtained for different thicknesses of the ion exchange diaphragm as well as for ion exchange diaphragms with different hydrodynamic permeability. If a diaphragm of the above-mentioned type with a thickness of 0.2 mm is used, for example, the pump output is, under otherwise equal conditions, about 25 $\mu$l/hr. for a pressure of 2.0 bar and a current $i = 0$ mA, corresponding to 0.6 ml/day. The pump output can also be influenced via the size of the ion exchange diaphragm.

In FIG. 3, the control behavior of the described embodiment of the dosing device is shown in a life test: Ag/AgCl-electrodes; area of the anion exchange diaphragm. 5 cm²; thickness, 0.6 mm; 0.9-% NaCl solution; pressure, 1.5 bar. It is clearly evident from the figure, in which the pump output v in $\mu$l/hr. or ml/day is plotted on the ordinate and the time t in hours on the abscissa, that the pump output can be varied greatly via the current. It was further found in the investigations that the main part of the output change takes place immediately after the current is changed. The control time constant is less than 5 minutes and the mean error of the pump output in continuous operation remains less than ±5%.

In FIG. 4, a cross section through an embodiment of the dosing device according to the invention of simplified design is shown. The dosing device 40 has inside a housing 41 merely a medicine reservoir 42 and a propellant chamber 44, which is separated therefrom by an elastic partition 43. The medicine reservoir 42 serves for receiving a physiological saline solution as the electrolyte, in which the medicine to be transported is dissolved. The medicine reservoir 42 is provided for this purpose with a replenishing opening 45, which is closed-off liquid-tight in a suitable manner. On the medicine reservoir 42, an electro-osmotic regulating valve 46 is arranged and connected to the former by canals 47. The control valve 46 consists of two porous electrodes 48, between which an ion exchange diaphragm 49 is arranged. Adjacent to that of the two electrodes 48 which is arranged on the side of the ion exchange diaphragm 49 facing away from the medicine reservoir 42, there is a small chamber 50 in which the medicine-electrolyte mixture passing through the ion exchange diaphragm 49 and the electrodes 48 is collected. This mixture leaves the chamber 50 through a discharge opening 51, which is advantageously closed-off by a porous plug.

The propellant chamber 44 of the embodiment of the dosing device according to FIG. 4 contains an electrolyte, preferably diluted sodium chloride solution. There are further provided in the propellant chamber two electrodes 53 and 54, which are separated from each other by a hydrophilic diaphragm, preferably an ion exchange diaphragm, for generating a gas serving as the propellant. The electrode 53, the anode, is a palladium-hydrogen electrode and the electrode 54, the cathode, is a platinum electrode. If the two electrodes are connected to an external current source, hydrogen is developed at the cathode 54, which serves as the propellant and displaces liquid, i.e., medication solution, from the medicine reservoir 42 via the elastic partition 43, preferably a silastic diaphragm.

What is claimed is:

1. An implantable dosing device for the continuous release of medication in the human or animal body, comprising a medicine reservoir of variable volume, a propellant chamber of variable volume tensionally connected to said medicine reservoir, and means for controlling the flow of said medication to the body, said means comprising an electro-osmotic regulating valve comprising an ion exchange diaphragm arranged between two porous electrodes, whereby liquid is transported through the electrodes and diaphragm when current flows.

2. An implantable dosing device according to claim 1 wherein the medicine reservoir is separated from the propellant chamber by an elastic partition and the electro-osmotic regulating valve is arranged at the medicine reservoir.

3. An implantable dosing device according to claim 1 wherein a liquid chamber of variable volume is provided between the propellant chamber and the medicine reservoir, separated from both the propellant chamber and the medicine reservoir by an elastic partition and, wherein the electro-osmotic regulating valve is arranged in the liquid chamber.

4. An implantable dosing device according to claim 1 wherein the porous electrodes of said electro-osmotic regulating valve are silver/silver chloride electrodes.

5. An implantable dosing device according to claim 1 wherein a volatile liquid is provided as the propellant in the propellant chamber.

6. An implantable dosing device according to claim 5, wherein said propellant is a low hydrocarbon-halogen compound.

7. An implantable dosing device according to claim 1 wherein the propellant chamber further contains an electrolyte and two electrodes separated by a hydrophilic diaphragm for generating a gas serving as the propellant.

8. An implantable dosing device according to claim 7, wherein at least one of the electrodes in the propellant chamber is a palladium-hydrogen electrode.

* * * * *